US012751982B2

(12) United States Patent
Park et al.

(10) Patent No.: US 12,751,982 B2
(45) Date of Patent: Oct. 6, 2026

(54) **BACTERIOPHAGE EFFECTIVE FOR CONTROLLING *SALMONELLA TYPHIMURIUM* AND ITS DERIVED BIOFILM, AND AN ANTIBACTERIAL COMPOSITION COMPRISING THE SAME**

(71) Applicant: KYUNGPOOK NATIONAL UNIVERSITY INDUSTRY-ACADEMIC COOPERATION FOUNDATION, Daegu (KR)

(72) Inventors: Mi-Kyung Park, Daegu (KR); Su-Hyeon Kim, Daegu (KR); Heejeong Lee, Busan (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 605 days.

(21) Appl. No.: 18/177,369

(22) Filed: Mar. 2, 2023

(65) Prior Publication Data

US 2023/0277610 A1 Sep. 7, 2023

(30) Foreign Application Priority Data

Mar. 2, 2022 (KR) ........................ 10-2022-0026924

(51) Int. Cl.
*A61K 35/76* (2015.01)
*A61P 31/04* (2006.01)

(52) U.S. Cl.
CPC .............. *A61K 35/76* (2013.01); *A61P 31/04* (2018.01); *C12N 2795/00031* (2013.01); *C12N 2795/10121* (2013.01); *C12N 2795/10131* (2013.01); *C12N 2795/10132* (2013.01)

(58) Field of Classification Search
None
See application file for complete search history.

(56) References Cited

U.S. PATENT DOCUMENTS

2012/0156174 A1* 6/2012 Yang ...................... A61K 35/76 435/235.1

FOREIGN PATENT DOCUMENTS

KR 10-2341100 B1 12/2021

OTHER PUBLICATIONS

KMB 2023, 48th Annual Meeting & International Symposium, The Korean Society for Microbiology and Biotechnology, Characterization and Employment of a Novel Salmonella-Specific Phage Isolated from Slaughter Wastewater.

KoSFoP 2021, 42nd International Symposium and Annual Meeting, The New Normal Era : Food Innovation and the Next, Characterization and Application of a Novel Salmonella-specific phage as a Green Biocontrol Agent, P4-52.

Iman M. A. Abdelhadi, et al., "Discovery of Polyvalent Myovirus (vB_STM-2) Phage as a Natural Antimicrobial System to Lysis and Biofilm Removal of *Salmonella typhimurium* Isolates from Various Food Sources", Sustainability, 2021, vol. 13, No. 11602, pp. 1-21.

* cited by examiner

*Primary Examiner* — Grant C Currens
(74) *Attorney, Agent, or Firm* — Sughrue Mion, PLLC

(57) ABSTRACT

Provided are a bacteriophage KFS-ST3 having specific killing ability for *Salmonella typhimurium* and its derived biofilm, and a pharmaceutical composition for preventing or treating infectious diseases caused by *Salmonella,* including the bacteriophage. The bacteriophage KFS-ST3 of the present disclosure has specific killing ability for *Salmonella,* but does not kill beneficial bacteria and has excellent acid resistance and heat resistance, and thus may be not only used for the prevention or treatment of infectious diseases caused by *Salmonella typhimurium* and its derived biofilm, but also widely used in antibiotic compositions, feed additive compositions, disinfectants, or cleaning agents.

3 Claims, 6 Drawing Sheets

BACTERIOPHAGE EFFECTIVE FOR CONTROLLING *SALMONELLA TYPHIMURIUM* AND ITS DERIVED BIOFILM, AND AN ANTIBACTERIAL COMPOSITION COMPRISING THE SAME

CROSS-REFERENCE TO RELATED APPLICATIONS

This application is based on and claims priority from Korean Patent Application No. 10-2022-0026924, filed on Mar. 2, 2022, with the Korean Intellectual Property Office, the disclosure of which is incorporated herein in its entirety by reference.

TECHNICAL FIELD

The present disclosure relates to a novel bacteriophage effective for controlling *Salmonella typhimurium* and its derived biofilm, and an antibacterial composition including the same, and more particularly, to a novel bacteriophage KFS-ST3 that has effective control ability for *Salmonella typhimurium* and its derived biofilm; a feed additive composition, a feed, a disinfectant or cleaning agent, and an antibiotic composition including the bacteriophage, and a method for preventing or controlling infectious diseases caused by *Salmonella typhimurium* and biofilms thereof, including administering the bacteriophage to a subject.

BACKGROUND

*Salmonella* is a gram-negative facultative anaerobic bacterium belonging to the family Enterobacteriaceae and a *Bacillus* that does not form spores, and a pathogenic microorganism widely distributed in nature as well as in the intestines of humans, animals and birds. *Salmonella* is a zoonotic pathogen that may be infected not only in humans but also in various livestock including pigs, cows, and chickens to cause diseases. When infecting humans, *Salmonella* causes food poisoning, which causes diarrhea, vomiting, abdominal pain, fever, and even chronic diseases such as arthritis, and in livestock such as pigs, cows and chickens, *Salmonella* causes Salmonellosis to develop acute and chronic infections, but is mainly infected by factors such as contaminated feed, and water. *Salmonella* spp. is classified into two major species of *S. enterica* and *S. bongori,* and most of the genus is *S. enterica,* which is classified into six subspecies according to biochemical characteristics. After identifying *Salmonella* species through biochemical tests and identifying serovars according to Kauffmann-White's antigen table, the strain name of *Salmonella* spp. was finally indicated, and about 2,659 serovars have been reported to date. Among them, the main serovars associated with food poisoning include *S. enteritidis, S. typhimurium, S. typhi,* and the like and are mainly caused by infection with meat, eggs, or fresh food.

Some *Salmonella* form biofilms to adapt to an environment in difficult conditions to survive, and the biofilm consists of microbial cells and extracellular polymeric materials such as polysaccharides, nucleic acids and proteins produced by these microbial cells during culture. The formed biofilm is hardly removed as the biofilm is strongly attached to various surfaces such as food, and stainless steel during the processing process, and has high resistance to processes such as heating and washing, harsh environments (pH, temperature, etc.), and antibiotics, due to a unique physiological and physical matrix barrier of the biofilm so that there is a problem in the food processing process. Accordingly, infections associated with the biofilms are hardly treated, and sessile bacteria in the biofilms are stronger resistant to antibiotics than planktonic bacteria, thereby not only making it difficult to control with conventional antibiotic therapy, but also causing serious problems in industry and medicine as a whole. As a result, research on a composition for inhibiting biofilm formation, a method for inhibiting biofilm formation, and the like is required.

Currently, chemical agents including antibiotics have been mainly used to prevent and control *Salmonella* infections and their derived biofilms, but when *Salmonella* infects animals, *Salmonella* often penetrates into cells to proliferate and infect, so that it is difficult for antibiotics, drugs, and other probiotics to penetrate and act. In addition, recently, problems with antibiotic resistance have occurred in many fields, and the cause thereof has been identified as the misuse or abuse of antibiotics, and antibiotics have not been used sufficiently. In addition, as consumer demands for safe food and food safety are increasing, the use of antibiotics is gradually decreasing. As a countermeasure against the problems, research on biological control technology has attracted attention, and in particular, technology using bacteriophages that specifically and effectively kill bacteria has been in the spotlight.

The bacteriophage is a virus that suppresses and inhibits the growth of infected bacteria by specifically infecting bacteria, and has higher host specificity than antibiotics and is relatively stable against environmental factors such as temperature and pH. The bacteriophage mainly has lysogenic and lytic life cycles, but among them, the lytic bacteriophage infects bacteria, replicates and assembles a genetic material inside a bacterial cell, and then destroys the cell wall of the host bacteria when progeny bacteriophages are released out of the bacteria, which is different from a mechanism of existing synthetic antibiotics. Accordingly, there are advantages of exhibiting antibacterial activity regardless of sensitivity to existing synthetic antibiotics and having antibacterial activity even in the control of biofilms formed by microorganisms. In addition, inventions using bacteriophages are superior in terms of shorter development time and less development costs than antibiotics, and high specificity, durability, and side effects.

Therefore, the present inventors paid attention to the development of technologies related to the isolation and purification of bacteriophages and their applications, in order to control *Salmonella* and its derived biofilm using a bacteriophage with excellent specificity and lytic activity, and be effectively used for the prevention and treatment of infections caused thereby. As a result, the present inventors isolated and purified a phage capable of specifically killing only *Salmonella* strains of various serovars from various samples, and named the phage as KFS-ST3. In addition, the present inventors identified the phage KFS-ST3 that had high bactericidal and bacteriostatic effects on *Salmonella* spp., temperature and pH stability through a characteristic examination experiment for KFS-ST3 and belonged to family Ackermannviridae taxonomically. Accordingly, the present inventors identified a novel bacteriophage through genetic analysis, and then completed the present disclosure.

SUMMARY

The present disclosure has been made in an effort to provide a novel bacteriophage KFS-ST3 having specific control ability for *Salmonella typhimurium* and a biofilm formed by *Salmonella typhimurium.* The present disclosure has also been made in an effort to provide an antibiotic composition, a feed additive composition, a feed, a disinfectant or a cleaning agent including the bacteriophage KFS-ST3.

An exemplary embodiment of the present disclosure provides a novel bacteriophage KFS-ST3 (accession number KCTC 14872BP) having specific killing ability for *Salmonella typhimurium* and its derived biofilm.

In an exemplary embodiment of the present disclosure, the bacteriophage may have additional killing ability against *Salmonella enteritidis, Salmonella* Mission, *Salmonella* Hartford and *Salmonella* Senftenberg, but is not limited thereto.

In an exemplary embodiment of the present disclosure, the bacteriophage may have the lytic activity in the range of pH 3.0 to pH 11.0, but is not limited thereto.

In an exemplary embodiment of the present disclosure, the bacteriophage may have the lytic activity in the range of −20° C. to 60° C., but is not limited thereto.

Another exemplary embodiment of the present disclosure provides an antibiotic composition including the bacteriophage KFS-ST3 as an active ingredient.

Yet another exemplary embodiment of the present disclosure provides a feed additive composition including the bacteriophage KFS-ST3 as an active ingredient.

Still another exemplary embodiment of the present disclosure provides a disinfectant including the bacteriophage KFS-ST3 as an active ingredient.

Still yet another exemplary embodiment of the present disclosure provides a cleaning agent including the bacteriophage KFS-ST3 as an active ingredient.

Still yet another exemplary embodiment of the present disclosure provides a pharmaceutical composition for preventing or treating infectious diseases caused by *Salmonella,* including the bacteriophage KFS-ST3 as an active ingredient.

Still yet another exemplary embodiment of the present disclosure provides a method for preventing or treating infectious diseases caused by *Salmonella,* including administering the pharmaceutical composition to a subject other than a human.

According to the exemplary embodiments of the present disclosure, the bacteriophage KFS-ST3 has an effect of specifically killing *Salmonella typhimurium* and its derived biofilm.

The bacteriophage KFS-ST3 has advantages of having very high specificity for *Salmonella* compared to chemicals such as conventional antibiotics, and having excellent lytic activity and being strong against physicochemical stimulation by infecting and proliferating *Salmonella.*

In addition, the bacteriophage KFS-ST3 has excellent acid resistance and heat resistance to be not only used as a material for preventing or treating infectious diseases caused by *Salmonella typhimurium* and its derived biofilm in various temperature and pH ranges, but also used as an antibiotic, a feed additive, a disinfectant or a cleaning agent including the bacteriophage KFS-ST3 as an active ingredient.

In addition, the bacteriophage KFS-ST3 or an antibiotic including the bacteriophage KFS-ST3 as an active ingredient is provided to have an advantage of solving a problem of antibiotic-resistant bacteria, a problem of residual antibiotics in food, and a problem of a wide range of hosts.

Accordingly, the bacteriophage KFS-ST3 of the present disclosure can be variously used in fields of prevention or treatment of infectious diseases caused by *Salmonella typhimurium* or its derived biofilm, an antibiotic composition, a feed additive composition, a feed, a disinfectant or a cleaning agent.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
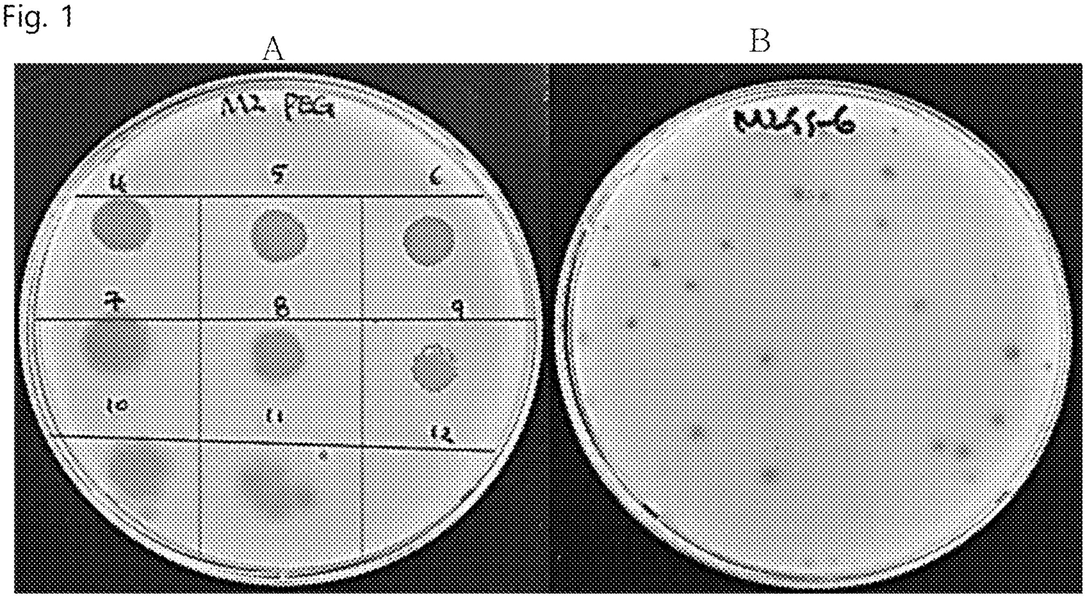
FIG. 1 is a diagram illustrating the plaque-forming activity of a bacteriophage KFS-ST3 against *Salmonella typhimurium* in an exemplary embodiment of the present disclosure.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, an exemplary embodiment of the present disclosure will be described in detail with reference to the accompanying drawings. However, the following exemplary embodiments are presented as examples for the present disclosure, and when it is determined that a detailed description of well-known technologies or configurations known to those skilled in the art may unnecessarily obscure the gist of the present disclosure, the detailed description thereof may be omitted, and the present disclosure is not limited thereto. Various modifications and applications of the present disclosure are possible within the description of claims to be described below and the equivalent scope interpreted therefrom.

Terminologies used herein are terminologies used to properly express embodiments of the present disclosure, which may vary according to a user, an operator's intention, or customs in the art to which the present disclosure pertains. Accordingly, definitions of the terminologies need to be described based on contents throughout this specification. Throughout the specification, when a part "comprises" a certain component, it is meant that the part may further include other components, not excluding other components, unless explicitly described to the contrary.

Throughout this specification, '%' used to indicate the concentration of a specific material is solid/solid (w/w) %, solid/liquid (w/v) %, and liquid/liquid (v/v) %, unless otherwise stated.

A bacteriophage KFS-ST3 of the present disclosure is a bacteriophage isolated by taking a sample from slaughter wastewater of a slaughterhouse in Gunwi, Gyeongsangbuk-do, which was named as a bacteriophage KFS-ST3 and patent-deposited with the accession number KCTC 14872BP at the Korean Collection for Type Cultures on Feb. 23, 2022.

The present disclosure provides a bacteriophage KFS-ST3 having the accession number KCTC 14872BP, which has specific killing ability for *Salmonella typhimurium* and its derived biofilm.

In the present disclosure, the term "bacteriophage" is a bacteria-specific virus that infects a specific bacterium to suppress and inhibit the growth of the bacterium, and refers to a virus containing single or double-stranded DNA or RNA as a genetic material.

The bacteriophage KFS-ST3 of the present disclosure has excellent lytic activity against *Salmonella typhimurium* and its derived biofilm, and it was confirmed that the bacteriophage KFS-ST3 belonged to family Ackermannviridae, which had an icosahedral head and a tail. In addition, the bacteriophage KFS-ST3 has excellent stabilities to heat and pH.

The specific lytic activity, acid resistance, basic resistance and heat resistance for *Salmonella typhimurium* and its derived biofilm as described above enable applications in various temperature and pH ranges, when the bacteriophage KFS-ST3 of the present disclosure is applied to the composition for preventing and treating infectious diseases caused by *Salmonella typhimurium* and its derived biofilm, and various products including the bacteriophage KFS-ST3 as the active ingredient.

The bacteriophage KFS-ST3 of the present disclosure maintains the lytic activity in the range of pH 3.0 to pH 11.0, but is not limited thereto.

The bacteriophage KFS-ST3 of the present disclosure maintains the lytic activity in the range of −20° C. to 60° C., but is not limited thereto.

In addition, the present disclosure provides a pharmaceutical composition for preventing or treating infectious diseases caused by *Salmonella,* including the bacteriophage KFS-ST3.

Further, the present disclosure provides an antibiotic composition including the bacteriophage KFS-ST3.

In the present disclosure, the term "antibiotic composition" means a preparation that is provided to animals in the form of a drug to kill bacteria, and is a generic term for preservatives, bactericides, antibiotics and antibacterial agents.

Since the bacteriophage KFS-ST3 of the present disclosure has higher specificity for infectious diseases against *Salmonella* than conventional antibiotics, the bacteriophage KFS-ST3 does not kill beneficial bacteria, but may kill only specific pathogens, and does not induce drug resistance, so as to be used as a novel antibiotic with a longer life cycling than conventional antibiotics.

The bacteriophage of the present disclosure is characterized by including the antibacterial activity against strains belonging to *Salmonella.* More specifically, the bacteriophage has the antibacterial activity against strains belonging to *Salmonella* spp., but is not limited thereto. However, in an exemplary embodiment of the present disclosure, it was confirmed that the bacteriophage has the lytic activity against *S. enteritidis, S. mission, S. hartford, S. senftenberg,* and *S. typhimurium* among the *Salmonella* strains, and particularly, has the most excellent lytic activity against *Salmonella typhimurium.* The *Salmonella* are characterized as strains that have pathogenicity to cause diseases such as food poisoning when infected. That is, the bacteriophage of the present disclosure is characterized by having the antibacterial activity against *Salmonella,* particularly pathogenic *Salmonella.*

Further, the present disclosure provides a feed additive composition including the bacteriophage KFS-ST3.

The feed additive antibiotics used in livestock and fisheries are used for preventing diseases, but antibiotic administration for prevention has become a problem in that the possibility of resistant bacteria is increased and the antibiotics remaining in livestock may be transmitted to humans, and when the antibiotics are absorbed into the human body through meat, the antibiotic resistance may cause to lead to the spread of diseases. In addition, there are many types of antibiotics mixed and taken with the feed to have a problem of increasing the probability of multi-drug resistant bacteria. As a new feed additive antibiotic that is eco-friendly and also solves problems caused by the use of existing antibiotics, the bacteriophage KFS-ST3 of the present disclosure may be used.

Other non-pathogenic microorganisms may be additionally added to the feed additive composition of the present disclosure. The microorganisms to be added may be selected from the group consisting of *Bacillus* such as *Bacillus subtilis,* capable of producing proteolytic enzymes, lipolytic enzymes and sugar converting enzymes, *Lactobacillus* strains (*Lactobacillus* spp.) with physiological activity and organic material decomposition ability under anaerobic conditions such as the stomach of cattle, filamentous fungi such as *Aspergillus oryzae,* which have effects of increasing the body weight of livestock, increasing milk production, and increasing the digestion-absorption rate of the feed, and yeasts such as *Saccharomyces cerevisiae.*

The feed including the bacteriophage KFS-ST3 of the present disclosure includes grains, root fruits, food processing by-products, algae, fibers, pharmaceutical by-products, oils and fats, starches, meal, grain by-products, etc. as vegetable products, and proteins, inorganic materials, oils, minerals, oils, single-celled proteins, zooplankton, leftover food, etc. as animal products, but is not limited thereto.

The feed additive composition of the present disclosure may include a binder, an emulsifier, a preservative, etc. added to prevent quality deterioration, and may include amino acids, vitamins, enzymes, probiotics, flavoring agents, non-protein nitrogen compounds, silicates, buffers, coloring agents, extractants, oligosaccharides, etc. added to the feed to increase efficacy, and may further include feed mixtures, etc.

Further, the present disclosure provides a disinfectant including the bacteriophage KFS-ST3.

The disinfectant including the bacteriophage KFS-ST3 of the present disclosure having the specific killing ability for

*Salmonella* may be usefully used as a hospital and health disinfectant to prevent hospital infection, and may be used for general life disinfectants, disinfectants for food and cooking places and facilities, disinfection of various growing products such as buildings such as farms, livestock, drinking water, litter, egg seats, transport vehicles, and tableware.

Further, the present disclosure provides a cleaning agent including the bacteriophage KFS-ST3.

Since the bacteriophage KFS-ST3 of the present disclosure has the specific killing ability for *Salmonella,* the bacteriophage KFS-ST3 may also be used for cleaning the skin surface, each body part, and the like of animals which have been exposed to or likely to be exposed to *Salmonella.*

Further, the present disclosure provides a method for preventing or treating infectious diseases caused by *Salmonella,* including administering the bacteriophage KFS-ST3 to a subject.

The bacteriophage KFS-ST3 of the present disclosure has specific killing ability for *Salmonella* to be used for preventing or treating infectious diseases caused by *Salmonella.*

In the present disclosure, the infectious diseases caused by *Salmonella* include symptoms caused by the diseases, such as common food poisoning symptoms such as abdominal pain, diarrhea, vomiting, fever, and headache. In addition, the infectious diseases include central nervous system symptoms such as sepsis, encephalitis and meningitis, and brain abscess in the case of pregnant women, infants, the elderly, and patients with reduced immune capacity.

The term "subject" of the present disclosure may include all animals other than humans, and preferably refers to mammals or fish, but is not limited thereto.

The term "prevention" of the present disclosure means any action that suppresses the disease or delays the onset of the disease by administering the composition.

The term "treatment" of the present disclosure refers to any action that improves the symptoms of the disease or inhibits or alleviates the disease and changes beneficially the disease by the administration of the composition.

The term "livestock" of the present disclosure is a concept that refers to useful animals that have been domesticated and improved by humans and live together with humans, and includes, for example, pigs, cattle, chickens, horses, ducks or dogs, but is not limited thereto.

It is obvious to those skilled in the art that an appropriate total daily amount of the bacteriophage KFS-ST3 administered in the method of the present disclosure may be determined by treatment within the scope of sound medical judgment. However, a therapeutically effective dose for a specific subject may vary depending on various factors including the kind and degree of the response to be achieved, the age, body weight, general health conditions, sex, and diet of an animal, an administration time, an administration route, a distribution rate of the composition, a duration of treatment, and other drugs used in combination or simultaneously with a specific composition, and similar factors well known in the medical field.

The pharmaceutical composition of the present disclosure includes $10^3$ to $10^{10}$ PFU/ml of the bacteriophage, preferably $10^6$ to $10^9$ PFU/ml of the bacteriophage. As used herein, the term "plaque forming unit (PFU)" is a unit for quantifying plaques that appear after the bacteriophage kills bacteria.

The pharmaceutical composition of the present disclosure may further comprise a pharmaceutically acceptable carrier.

In the present disclosure, the term "pharmaceutically acceptable carrier" may refer to a carrier or a diluent which does not inhibit the biological activity and properties of a compound to be administered without stimulating organisms. In the composition formulated with a liquid solution, the pharmaceutically acceptable carrier is suitable for sterilization and living bodies, and may use saline, sterilized water, ringer's solution, buffered saline, albumin injection solution, dextrose solution, maltodextrin solution, glycerol, ethanol, and a mixture of at least one of these ingredients, and if necessary, may add other general additives such as antioxidants, buffers, and bacteriostatic agents. In addition, the composition may be prepared in injectable formulations such as aqueous solutions, suspensions, and emulsions, pills, capsules, granules, or tablets by further adding a diluent, a dispersant, a surfactant, a binder, and a lubricant.

Terms not defined otherwise in this specification have meanings commonly used in the technical art to which the present disclosure pertains.

Hereinafter, the present disclosure will be described in detail by Example Embodiments and Preparation Examples. However, the following Example Embodiments and Preparation Examples are just illustrative of the present disclosure, and the contents of the present disclosure are not limited to the following Example Embodiments and Preparation Examples.

EXAMPLE EMBODIMENT 1

Isolation and Culture of Novel Bacteriophage 1-1. Screening of Bacteriophages Infected with *Salmonella typhimurium* and Isolation of Single Bacteriophages In order to screen and isolate bacteriophages specific to *Salmonella typhimurium* from a sample, a soft agar overlay method was performed. The soft agar overlay method was a method of analyzing the presence or absence of bacteriophages through the formation of plaques by mixing and culturing the sample and a host strain. More specifically, 25 ml of slaughter wastewater obtained from a slaughterhouse in Gunwi, Gyeongsangbuk-do was prepared as a sample, mixed with the host strain, and incubated. Thereafter, the host strain was mixed with a top-agar (0.4%) medium, dispensed and incubated on a solid medium, and the incubated sample liquid was dropped thereon to observe the formation of the incubated plaques.

Specifically, 225 ml of a TSB medium was mixed with 25 ml of the sample (liquid) and 1% of a *Salmonella typhimurium* ATCC 13311 shaking culture medium ($OD_{640}$=0.353) and incubated at 37° C. for 18 hours, and then the culture solution was centrifuged at 8,000 rpm for 10 minutes, and the supernatant was filtered through a 0.25 μm filter. Then, a mixture of 4 ml of TA soft agar (0.4% (w/v) agar, nutrient medium, NaCl, $MgSO_4$, $CaCl_2$) and 200 μl of the *Salmonella typhimurium* ATCC 13311 shaking culture medium ($OD_{640}$=0.353) was poured and solidified on the top of a TSA plate medium, and then 10 μl of the sample solution was dropped thereon and incubated at 37° C. for 18 hours, and then the presence or absence of bacteriophages was confirmed by checking whether a clear zone was formed.

As illustrated in A of FIG. 1, the presence of bacteriophages was confirmed by confirming the formation of plaques, and the bacteriophage was a bacteriophage having specific lytic ability to *Salmonella typhimurium.* In addition, a single bacteriophage was intended to be isolated from the formed plaques. Specifically, the plaques was placed in 900 μl of a sodium chloride-magnesium sulfate (SM) buffer (50 mM Tris-HCl, 100 mM NaCl, 10 mM $MgSO_4$, pH 7.5) and then left at room temperature for 2 hours to obtain a bacteriophage solution. Plaque assay was repeated with the bacteriophage solution obtained above, and such a process was repeated at least 10 times until the sizes and shapes of the plaques formed were similar to each other to isolate a single bacteriophage. The result of confirming the formation of plaques of the isolated single bacteriophage was illustrated in B of FIG. 1.

1-2. Mass Culture and Purification of Bacteriophage

In order to mass-culture bacteriophages specific to *Salmonella typhimurium* identified in Example Embodiment 1-1, *Salmonella typhimurium* ATCC 13311 was incubated in large quantities, and bacteriophages were purified therefrom.

Specifically, a host strain (*Salmonella typhimurium* ATCC 13311) was incubated with shaking and dispensed into 3 ml of a TA culture medium (nutrient broth, NaCl, $MgSO_4$, $CaCl_2$), and then incubated at 37° C. for 2 hours. The bacteriophages obtained in Example Embodiment 1.1 were dispensed and incubated for 2 hours, and then centrifuged and filtered to isolate only the bacteriophages. In the same manner, the amount of the TA culture medium was increased (in the order of 8, 20, 200, and 800 ml). Thereafter, the mixture was added with polyethylene glycol (PEG) and 1 M NaCl to have a final concentration of 10% (w/v), left at 4° C. for 16 hours, and then centrifuged at 4° C. and 8,000 rpm for 20 minutes to obtain a precipitate.

The purified phages were subjected to CsCl density gradient ultracentrifugation (density gradient: 1.20, 1.30, 1.40, 1.45, 1.50, 1.70 g/ml; 22,000 rpm; 2 hours; 4° C.), dialyzed in an SM buffer solution (50 mM Tris-HCl, 100 mM NaCl, 10 mM $MgSO_4$) and stored in a dark place at 4° C. until use.

The isolated bacteriophage was named "bacteriophage KFS-ST3" and deposited at the Korean Collection for Type Cultures, Korea on Feb. 23, 2022 and given the accession number KCTC 14872BP.

EXAMPLE EMBODIMENT 2

Morphological Characteristics of Bacteriophage KFS-ST3

In order to examine the morphological characteristics of the bacteriophage KFS-ST3, transmission electron microscopic observation was performed. The bacteriophage KFS-ST3 was loaded onto a copper grid, and then negatively stained with 2% uranyl acetate and dried. Electron microscopy was performed in a collaborating laboratory at Kyungpook National University, and the form of the bacteriophage KFS-ST3 was observed at a voltage of 100 kV using H-7100 (Hitachi), and the results were illustrated in FIG. 2.

Figure 2:
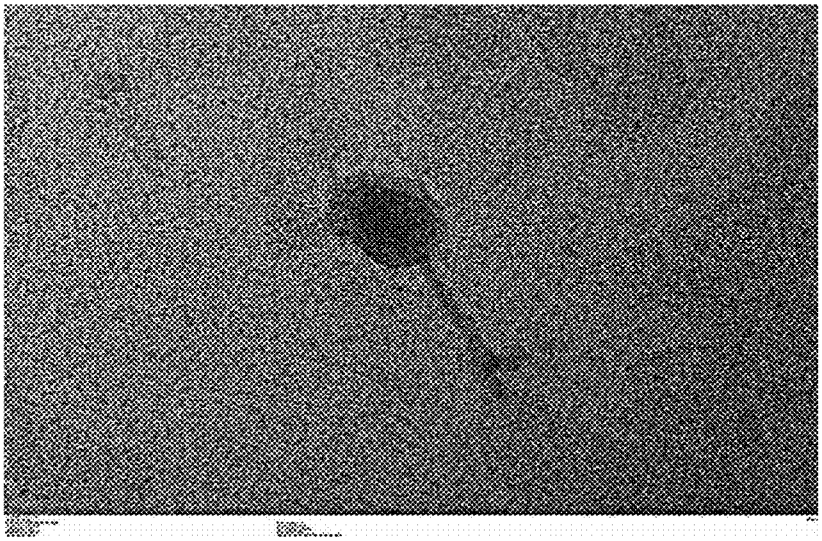
FIG. 2 is a diagram of confirming the morphological characteristics of the bacteriophage KFS-ST3 through an electron microscope in an exemplary embodiment of the present disclosure.

As illustrated in FIG. 2, since an icosahedral head and a contractile tail were observed in the bacteriophage KFS-ST3, it was assumed to have morphological characteristics of Myovirus.

EXAMPLE EMBODIMENT 3

Examination of Temperature Stability of Bacteriophage KFS-ST3

In order to confirm the temperature stability of the bacteriophage KFS-ST3, in various temperature ranges (−70° C., −20° C., −10° C., 4° C., 10° C., 20° C., 30° C., 40° C., 50° C., 60° C., and 70° C.), the lytic activity of KFS-ST3 was measured.

Specifically, 100 μl of a bacteriophage KFS-ST3 solution at a concentration of $1.03\times10^8$ PFU/ml was mixed with 900 μl of a TSB medium solution, and then left at room temperature for 1 hour in each temperature (−70° C., −20° C., 4° C., 10° C., 25° C., 37° C., 50° C., 60° C., and 70° C.). The KFS-ST3 reacted for one hour was incubated at 37° C. for 18 hours using a soft agar overlay method, and then the activity of the remaining bacteriophage KFS-ST3 was measured. The result was illustrated in FIG. 3.

Figure 3:
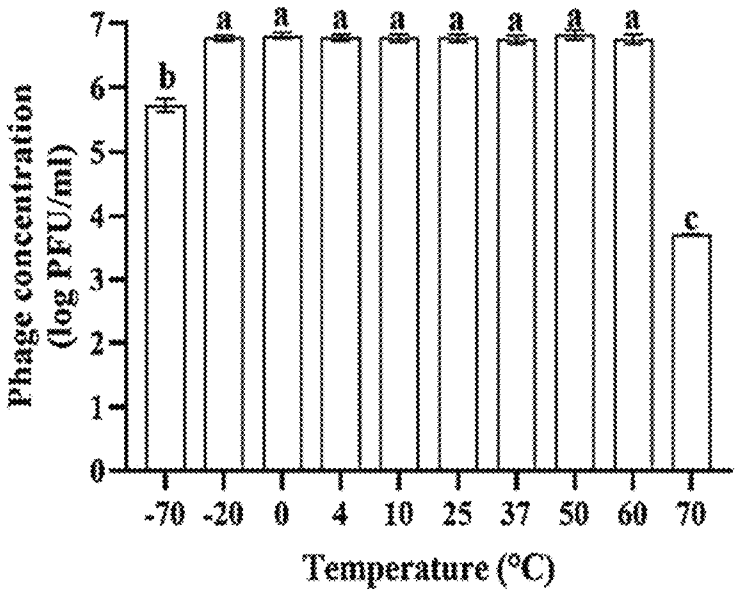
FIG. 3 is a diagram illustrating a result of examining the temperature stability of the bacteriophage KFS-ST3 in an exemplary embodiment of the present disclosure.

As illustrated in FIG. 3, it could be seen that the lytic activity of the bacteriophage KFS-ST3 was stable at −20° C. to 60° C., and reduced by about 1 log at −70° C. and by about 3 log at 70° C.

Accordingly, since the bacteriophage KFS-ST3 of the present disclosure was a bacteriophage with relatively excellent heat resistance, it was confirmed that when used as a feed additive or an antibacterial composition, the bacteriophage KFS-ST3 might be formulated stably against heat generated during the formulation process of the bacteriophage.

EXAMPLE EMBODIMENT 4

Examination of pH Stability of Bacteriophage KFS-ST3

In order to confirm the pH stability of the bacteriophage KFS-ST3, 100 μl of the bacteriophage KFS-ST3 at a concentration of $1.03\times10^8$ PFU/ml was mixed with 900 μl of the TSB medium in various pH ranges (pH 1, 2, 3, 4, 5, 6, 7, 8, 9, 10, 11, and 12), and then left at room temperature for 1 hour. The KFS-ST3 reacted for one hour was incubated at 37° C. for 18 hours using a soft agar overlay method, and then the activity of the remaining bacteriophage KFS-ST3 was measured. The measurement result was illustrated in FIG. 4.

Figure 4:
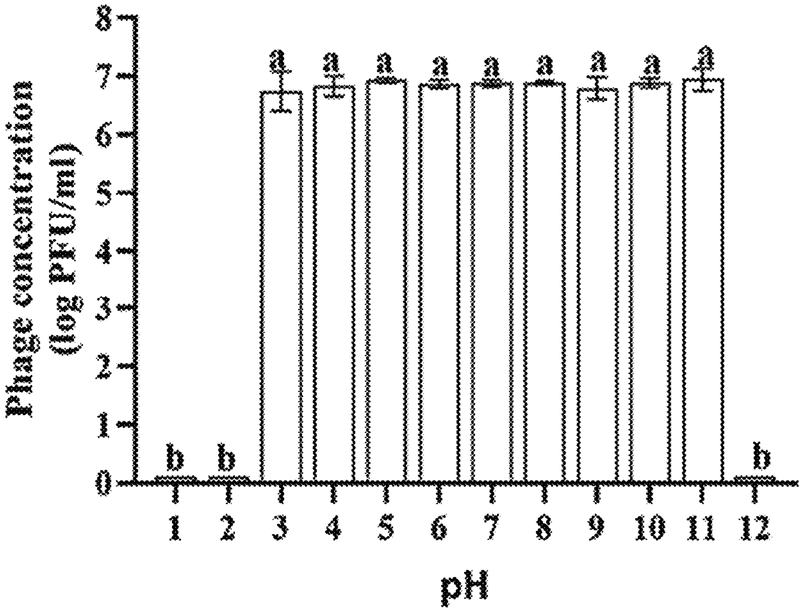
FIG. 4 is a diagram illustrating a result of examining the pH stability of the bacteriophage KFS-ST3 in an exemplary embodiment of the present disclosure.

As illustrated in FIG. 4, it was confirmed that the activity of the bacteriophage KFS-ST3 was stably maintained in the range of pH 3.0 to pH 11.0.

Accordingly, since it was confirmed that the activity of the bacteriophage KFS-ST3 of the present disclosure was maintained in the range of pH 3.0 to 11.0, it was confirmed that the bacteriophage had excellent pH stability.

EXAMPLE EMBODIMENT 5

Challenge Assay Analysis of Bacteriophage KFS-ST3

Figure 5:
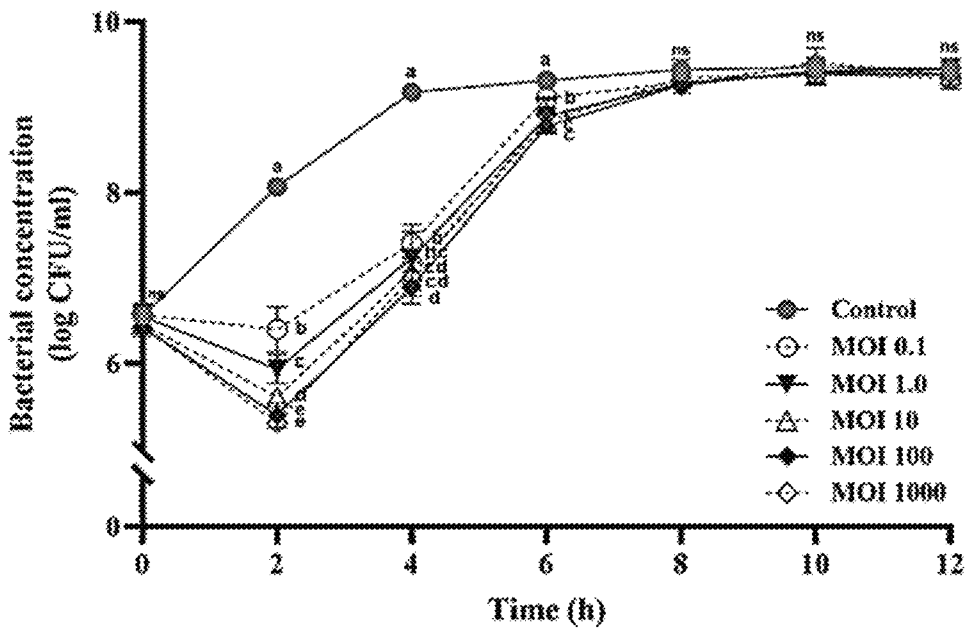
FIG. 5 is a diagram illustrating a challenge assay result of examining the bactericidal and bacteriostatic effects of the bacteriophage KFS-ST3 on *Salmonella typhimurium* in an exemplary embodiment of the present disclosure.

*Salmonella typhimurium* ATCC 13311 was inoculated into 100 ml of TSB and incubated for 3 hours at 37° C. at 190 rpm. When the absorbance value of the culture solution reached about 0.353 at 640 nm ($10^8$ CFU/ml), 1 ml of a KFS-ST3 suspension was adjusted to MOI of 0.1, 1, 10, and 100 and incubated at 37° C. at 110 rpm for 12 hours to confirm the bactericidal and bacteriostatic effects of the phage. The KFS-ST3 culture medium without adding *Salmonella* was used as a control. An initial bacterial concentration value was 6 Log CFU/mL after dilution, and viable cell counts were measured at 2-hour intervals, and the results were illustrated in FIG. 5.

As a result, the lytic activity was maintained for 8 hours at all of 0.1, 1, 10, and 100 regardless of the MOI. It was confirmed that the lytic activity of KFS-ST3 was the most active after 2 hours of phage treatment at MOI of 0.1, and the inhibition increased as the MOI increased, and in particular, the inhibition ability of about 2.4 log level was confirmed at MOI 1000.

EXAMPLE EMBODIMENT 6

Analysis of Biofilm Formation Ability of Host Strain of Bacteriophage KFS-ST3

Figure 6A:
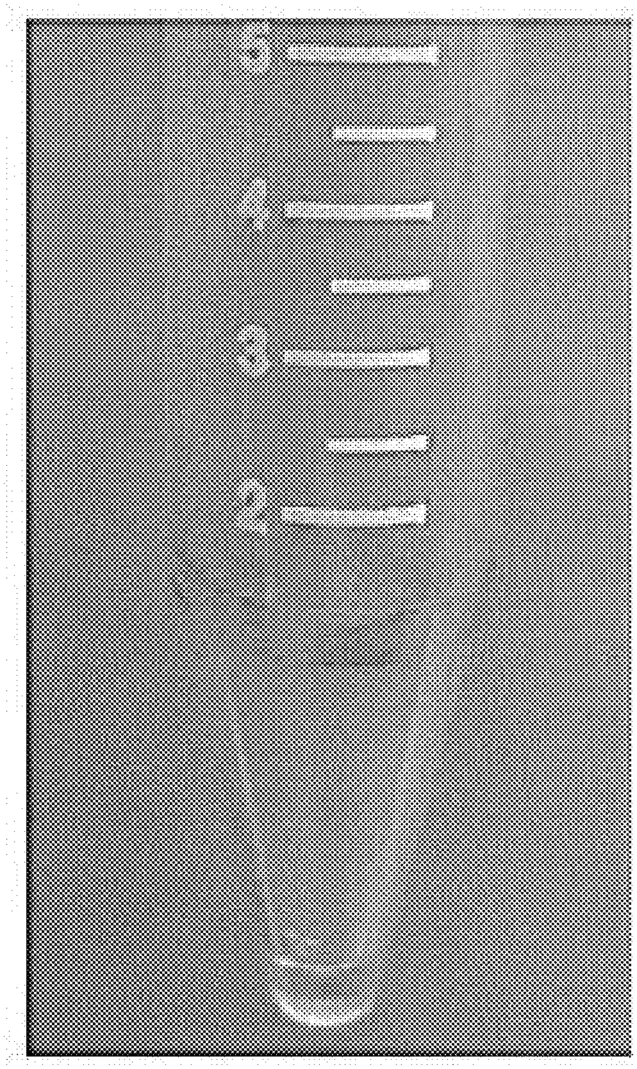
FIG. 6A and FIG. 6B are diagrams illustrating a result of examining the biofilm formation ability of *Salmonella typhimurium,* a host strain of the bacteriophage KFS-ST3, in an exemplary embodiment of the present disclosure.

The biofilm formation ability of *Salmonella typhimurium* ATCC 13311, which was a host strain of bacteriophage KFS-ST3, was analyzed. The *Salmonella typhimurium* ATCC 13311 was incubated to an absorbance value of 0.353 at 640 nm ($10^8$ CFU/ml), and then serially diluted to $10^6$ CFU/ml. An aliquot of 1 ml of the diluted *Salmonella typhimurium* culture solution was dispensed into a conical tube, and then static-incubated at 25° C. for 48 hours to form a biofilm. After incubation, the strain culture medium was removed, washed three times with 1 ml of PBS, and the conical tube was stained with 2 ml of 1% crystal violet for 15 minutes to confirm the biofilm formation, and the results were illustrated in FIG. 6A.

EXAMPLE EMBODIMENT 7

Analysis of Control Ability of Formed *Salmonella typhimurium* Biofilm by Bacteriophage KFS-ST3

Figure 6B:
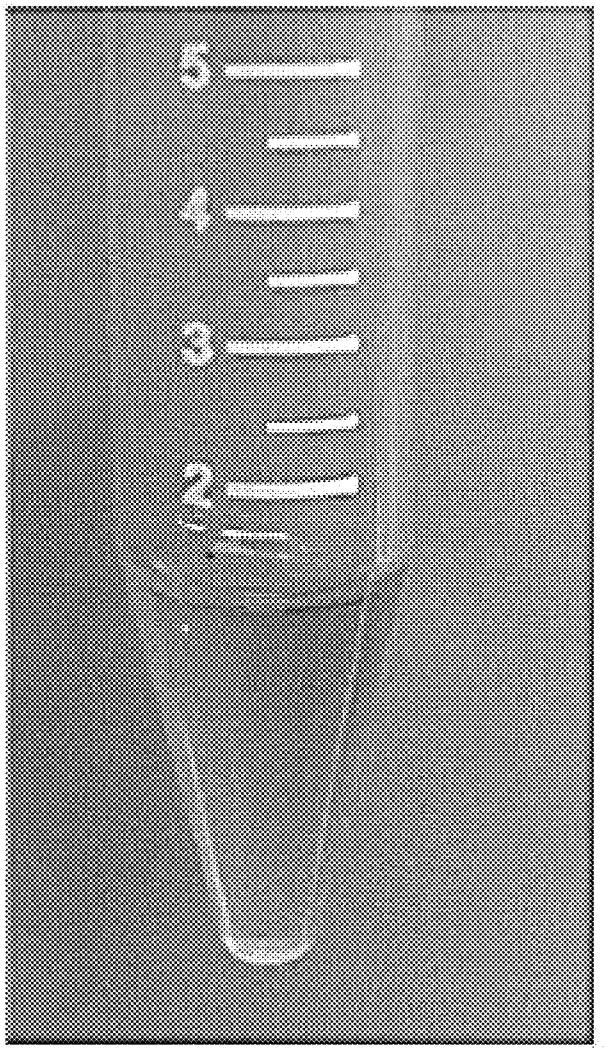

The biofilm control ability of KFS-ST3 was evaluated against biofilm of *Salmonella typhimurium* ATCC 13311, which was a host strain of the bacteriophage KFS-ST3 formed in Example Embodiment 6, formed on the polypropylene (PP) surface. More specifically, overnight culture of *Salmonella typhimurium* ATCC 13311 was submerged into the PP tube and incubated at 4° C. and 22° C. for 48 hours for biofilm formation. The formed biofilm was washed three times with 1 ml of phosphate buffered saline, and then the bacteriophage KFS-ST3 ($10^9$ PFU/ml) was dispensed into the PP tube formed with the biofilm, respectively, and incubated at 4° C. and 22° C. for 2 hours. In order to determine the biofilm control ability of KFS-ST3, the sample was first obtained at 30 minute intervals for 2 hours of incubation, the strain culture medium was removed, and then washed twice with PBS. The conical tube was stained with 2 ml of 1% crystal violet for 15 minutes and washed with sterile distilled water three times, and then the stained biofilm was dissolved with ethanol (FIG. 6B), and the absorbance (OD 600 nm) was measured to confirm the biofilm eradication ability of bacteriophage KFS-ST3.

In addition, in order to quantify *Salmonella typhimurium* surviving in the biofilm, in the same manner as the above method, 1 ml of PBS was dispensed into the PP tube from which the strain culture medium was removed every 30 minutes, and the biofilm was degraded by strongly vortexing for 5 minutes. Thereafter, in order to measure the number of viable bacteria in the degraded biofilm, the sample was diluted in decimal steps and spread on an XLD agar medium, then incubated at 37° C. for 24 hours to count the produced colonies, and the result was indicated by log CFU/ml.

Figure 7:
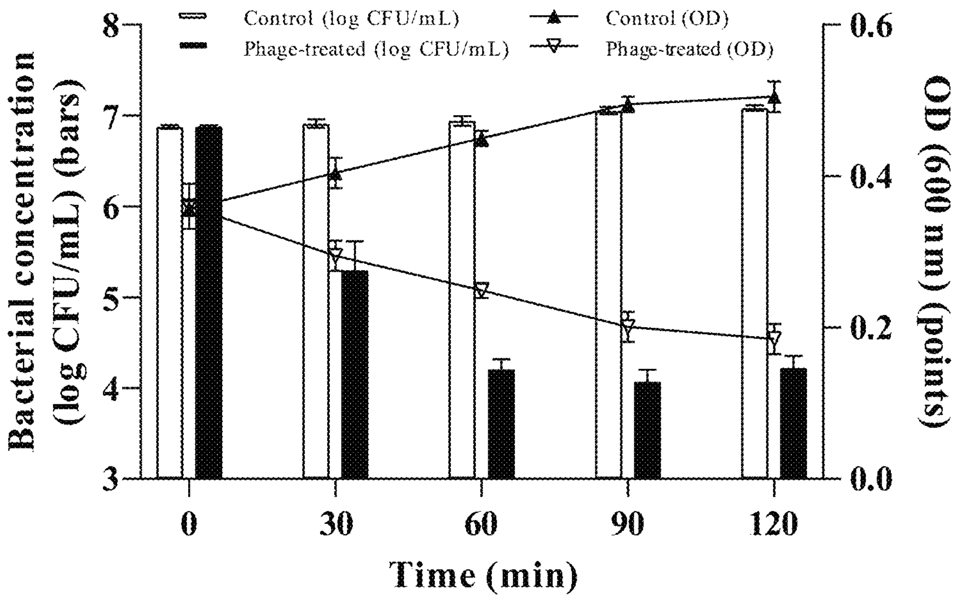
FIG. 7 is a diagram illustrating a result of examining the control ability of a formed *Salmonella typhimurium* biofilm on the polypropylene surface by the bacteriophage KFS-ST3 in an exemplary embodiment of the present disclosure.
Figure 8:
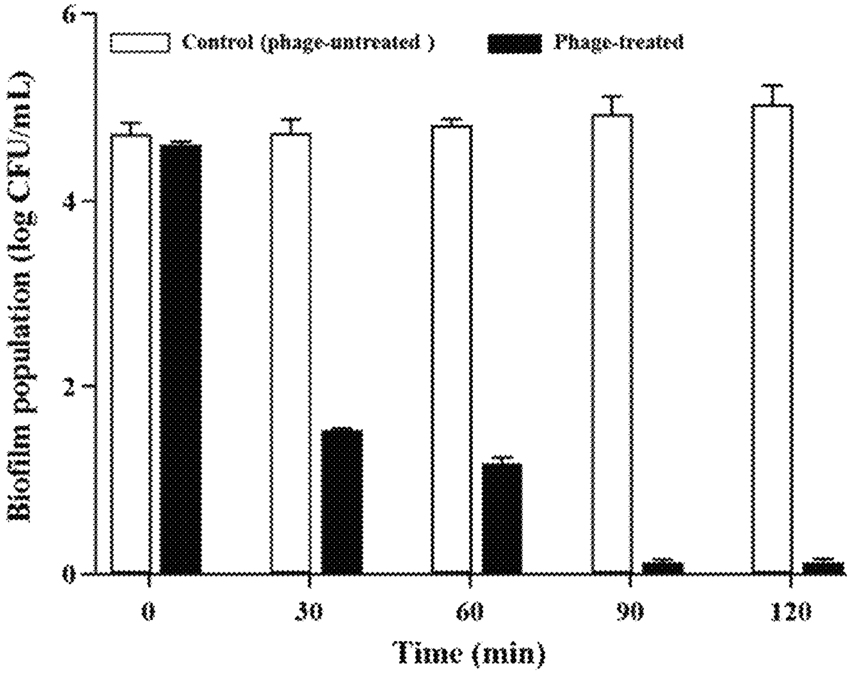
FIG. 8 is a diagram illustrating a result of examining the control ability of a formed *Salmonella typhimurium* biofilm on the polypropylene surface by the bacteriophage KFS-ST3 in an exemplary embodiment of the present disclosure.

As the experimental result, in results of observing the absorbance and measuring *Salmonella typhimurium* viable cell count in the biofilm, all results showed significantly lower results than the control at both temperatures (FIG. 7 and FIG. 8). After 1 hour of phage treatment at 22° C., *Salmonella typhimurium* in the biofilm was reduced by about 3 log CFU/mL (FIG. 7). In addition, 90-minutes treatment of bacteriophage KFS-ST3 reduced *Salmonella typhimurium* by about 4.5 log CFU/mL at 4° C. (FIG. 8). Particularly, KFS-ST3 treatment at 4° C. almost eradicated *Salmonella typhimurium* biofilm formed on the PP surface. Through this, it was confirmed that the *Salmonella typhimurium* biofilm was effectively removed by the KFS-ST3 treatment, and the result was illustrated in FIG. 7 and FIG. 8.

EXAMPLE EMBODIMENT 8

Examination of Specificity of Bacteriophage KFS-ST3 Against Pathogenic Strains

Specificity examination was performed to confirm the lytic activity of the bacteriophage KFS-ST3 against other pathogenic food poisoning strains other than *Salmonella.*

Specifically, *Salmonella* and 39 other foodborne pathogens were incubated, respectively, to obtain its culture medium, and then it was confirmed whether plaques were formed through a soft agar overlay method using each culture medium and bacteriophage KFS-ST3, and the results were shown in Table 1. As a result of the experiment, efficiency of plating (EOP) analysis was performed using plaque assay for strains formed with plaques. The EOP values were calculated through Equation 1 below.

EOP value=the number of plaques of test strain/the number of plaques of indicator strain (*Salmonella typhimurium* ATCC 13311) [Equation 1]

TABLE 1

| Strain name | Formation of plaques | EOP |
|---|---|---|
| *Salmonella Typhimurium* ATCC 13311 | O | 1.00 ± 0.00 |
| S. Hartford | O | 0.97 ± 0.05 |
| S. Mission | O | 0.89 ± 0.03 |
| S. Senftenberg | O | 0.86 ± 0.09 |
| S. Enteritidis ATCC 13076 | O | 0.83 ± 0.06 |
| S. Salamae | X | X |
| S. Dublin NCCP 13700 | X | X |
| S. Heidelberg NCCP 13698yphi | X | X |
| S. Montevideo NCCP 13704 | X | X |
| S. Newport NCCP 13686 | X | X |
| S. Panama NCCP 13694 | X | X |
| *Bacillus cereus* ATCC 13061 | X | X |
| *B. cereus* ATCC 14579 | X | X |
| *B. cereus* ATCC 1611 | X | X |
| *B. cereus* ATCC 21768 | X | X |
| *Citrobacter freundii* KCTC 2509 | X | X |
| *Escherichia coli* O157:H7 ATCC 10536 | X | X |
| *E. coli* ATCC 700599 | X | X |
| *E. coli* O157:H7 ATCC 43895 | X | X |
| *E. coli* ATCC BAA-2192 | X | X |
| E. coli ATCC BAA-2196 | X | X |
| *E. coli* NCCP 13581 | X | X |
| *E. coli* NCCP 15651 | X | X |
| *E. coli* NCCP 15732 | X | X |
| *E. fergusonii* KCTC 22525 | X | X |
| *Listeria monocytogenes* ATCC 7644 | X | X |
| *L. monocytogenes* ATCC 19116 | X | X |
| *L. innocua* ATCC 33090 | X | X |
| *Pseudomonas aeruginosa* ATCC 9207 | X | X |
| *Shigella boydii* NCCP 11190 | X | X |
| *S. flexoneri* 2457T | X | X |
| *S. sonnei* ATCC 9290 | X | X |
| *Staphylococcus aureus* ATCC 25923 | X | X |
| *S. aureus* KBN 10P00338 | X | X |
| *S. aureus* KBN 10P04941 | X | X |
| *Vibrio parahaemolyticus* ATCC 17802 | X | X |

TABLE 1-continued

| Strain name | Formation of plaques | EOP |
|---|---|---|
| *Yersinia enterocolitica* ATCC 23715 | X | X |
| *Y. enterocolitica* ATCC 55075 | X | X |

As shown in Table 1 above, it may be seen that the bacteriophage KFS-ST3 exhibits lytic activity against 5 *Salmonella* serovars including *S. enteritidis, S. mission, S. hartford, S. senftenberg,* and *S. typhimurium,* whereas it did not exhibit the lytic activity against other 34 bacterial strains. Accordingly, the bacteriophage KFS-ST3 had the lytic activity specifically against various serovars of *Salmonella,* and through the EOP results, the bacteriophage KFS-ST3 exhibited the highest lytic activity, especially for *Salmonella typhimurium.*

From the above experiment, it was confirmed that the method for preventing or treating infectious diseases caused by *Salmonella typhimurium* using the bacteriophage KFS-ST3 of the present disclosure had very high specificity for *Salmonella* compared to chemicals such as conventional antibiotics, had excellent lytic activity, was strong against physicochemical environments, and had the control ability of the biofilm derived from *Salmonella typhimurium.* In addition, the bacteriophage KFS-ST3 of the present disclosure has an advantage of being able to solve a problem of antibiotic-resistant bacteria due to misuse or abuse of antibiotics, a problem of residual antibiotics in food, and a problem of a wide range of hosts. Accordingly, the bacteriophage KFS-ST3 of the present disclosure may effectively prevent and treat infections caused by *Salmonella typhimurium* and its derived biofilm in aquaculture and livestock industries.

Hereinafter, Preparation Examples of the pharmaceutical composition for preventing or treating infectious diseases including the bacteriophage KFS-ST3 of the present disclosure will be described, but these Preparation Examples are intended to exemplarily explain Preparation Examples that may be prepared according to the present disclosure, and the scope of the present disclosure is not limited to these Preparation Examples.

PREPARATION EXAMPLE 1

Preparation of Pharmaceuticals 1-1. Preparation of Injections

Bacteriophage KFS-ST3 $1\times10^6$ PFU/ml

Sterile distilled water for injection Suitable amount pH adjusting agent Suitable amount The injections were prepared with the ingredient content per 1 ampoule (2 mL) according to a general method for preparing injections.

1-2. Preparation of Liquids

Bacteriophage KFS-ST3 $1\times10^6$ PFU/ml

Sugar 20 g

Isomerized sugar 20 g

Lemon flavor Suitable amount

Purified water was added to adjust the total to 1,000 ml, the ingredients were mixed according to a general method for preparing liquids, and then filled into a brown bottle and sterilized to prepare liquids.

1-3. Preparation of Tablets

Bacteriophage KFS-ST3 $1\times10^6$ PFU/ml

Corn starch 100 mg

Lactose 100 mg

Magnesium stearate 2 mg

The ingredients were mixed and then tableted according to a general method for preparing tablets to prepare tablets.

As described above, the present disclosure has been described as the preferred exemplary embodiments mentioned above, but those skilled in the art will be able to easily propose other degenerate inventions or other exemplary embodiments included in the scope of the present disclosure by adding, changing, or deleting other elements within the same technical scope. Therefore, the exemplary embodiments described above are illustrative in all respects and are not intended to limit the scope of the present disclosure.

Accession Number

Depositary Authority Name: Korean Collection for Type Cultures

Accession number: KCTC 14872BP

Accession Date: 20220223

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for treating an infectious disease caused by *Salmonella Typhimurium, Salmonella Hartford, Salmonella Mission, Salmonella Senftenberg, or Salmonella Enteritidis*, the method comprising administering an effective amount of a bacteriophage KFS-ST3 being deposited at the Korean Collection for Type Cultures (KCTC) under accession number KCTC 14872BP to a subject in need thereof.

2. The method of claim 1, wherein the bacteriophage has the lytic activity in the range of pH 3.0 to pH 11.0.

3. The method of claim 1, wherein the bacteriophage has the lytic activity in the range of −20° C. to 60° C.

* * * * *